(12) United States Patent
Schmitt

(10) Patent No.: US 8,037,592 B2
(45) Date of Patent: Oct. 18, 2011

(54) CASSETTE CHANGING DEVICE

(75) Inventor: Christoph Schmitt, Schriesheim (DE)

(73) Assignee: Leica Bisosystems Nussloch GmbH, Nussloch (DE)

( * ) Notice: Subject to any disclaimer, the term of this patent is extended or adjusted under 35 U.S.C. 154(b) by 572 days.

(21) Appl. No.: 12/247,712

(22) Filed: Oct. 8, 2008

(65) Prior Publication Data

US 2009/0146335 A1  Jun. 11, 2009

(30) Foreign Application Priority Data

Dec. 11, 2007 (DE) .......................... 10 2007 059 566

(51) Int. Cl.
*B21D 39/00* (2006.01)
*G01N 1/06* (2006.01)
(52) U.S. Cl. .......................................... 29/559; 264/158
(58) Field of Classification Search .................... 29/559, 29/721, 707, 709, 712, 281.1, 281.4; 264/158; 83/109, 409.1, 13
See application file for complete search history.

(56) References Cited

U.S. PATENT DOCUMENTS

| 2005/0235542 | A1 | 10/2005 | Metzner et al. | |
| 2009/0148264 | A1* | 6/2009 | Schmitt | 414/787 |
| 2010/0058913 | A1* | 3/2010 | Walter | 83/648 |

FOREIGN PATENT DOCUMENTS

| DE | 902 912 | 1/1954 |
| DE | 30 46 650 | 7/1982 |
| DE | 202004006265 | 7/2004 |
| DE | 603 00 921 | 12/2005 |
| WO | WO 02/090966 | 11/2002 |

OTHER PUBLICATIONS

German Examination Report dated Mar. 13, 2008.
German Examination Report, dated Mar. 13, 2008, for German priority application.
United Kingdom Search and Examination Report dated, Oct. 31, 2008, in related UK application.

* cited by examiner

*Primary Examiner* — John C Hong
(74) *Attorney, Agent, or Firm* — Nelson Mullins Riley & Scarborough, LLP

(57) ABSTRACT

A cassette changing device for a microtome has a housing having a loading opening, a transfer opening and an unloading opening. The openings are arranged with respect to each other linearly in the housing. A slide is disposed in the housing linearly movably between a first position and a second position and has a first receiving compartment and a second receiving compartment. The first and second compartments are aligned with respect to each other so that, in the first position of the slide, the first compartment and the second compartment are respectively aligned with a first two of the openings and, in the second position of the slide, the first compartment and the second compartment are respectively aligned with a second two of the openings.

10 Claims, 4 Drawing Sheets

CASSETTE CHANGING DEVICE

The invention relates to a cassette changing device, in particular for microtomes.

BACKGROUND OF THE INVENTION

DE 20 2004 006 265 U1 discloses a microtome which includes a magazine comprising a plurality of cassettes into which samples to be processed are embedded. The individual cassettes are supplied to the sample holder at the microtome with the aid of a gripper or displacer from the magazine and are returned into the same. Each time a cassette is to be supplied to the magazine, the magazine is displaced into such a position in which the desired cassette is located in the working area of the gripper or displacer. After the processed cassette has been returned, the magazine is displaced into a new position to supply the next cassette. The sequence of providing a cassette, supplying the sample to the cutting device, and returning the cassette into the magazine involves a certain amount of time.

With increasing automation of the work flow at the microtome, and with coding of the magazines and cassettes as described in DE 20 2004 006 265, it becomes possible to process the cassettes arranged in a magazine one after the other in the order of their placement in the magazine. While processing one cassette, the next cassette can be provided for processing, but this will block the return of the processed cassette into the magazine, so that the processed cassette would have to be manually removed from the sample holder at the microtome.

SUMMARY OF THE INVENTION

Accordingly, one object of one or more embodiments of the present invention is to allow an accelerated work flow without the need for a manual intervention in the cutting area.

This and other objects may be achieved by one or more embodiments described herein. In one embodiment of the present invention, a slide is equipped with two receiving compartments for the transfer of cassettes from an area of a supply magazine into an area of processing at the microtome. In a first position, a first receiving compartment can receive a cassette to be newly processed from the area of the supply magazine. Independent thereof, a cassette already processed at the microtome can be inserted into a second receiving compartment. By the additional possibility of traversing the slide at the processing station past the microtome and into a second position, a cassette for processing can be transferred to the microtome from the first receiving compartment, and the cassette returned into the second receiving compartment after processing can be unloaded into a collecting container for archiving or disposal. By reversing the slide with the now emptied receiving compartments into the first position, the changing steps can be arbitrarily repeated without manual intervention. The slide is suitably inserted into a housing having corresponding openings for receiving, transferring and unloading of cassettes. The housing can be mounted at the microtome at a suitable position for an automated work flow.

BRIEF DESCRIPTION OF THE DRAWINGS

A disclosure of the present invention is set forth in this specification, which makes reference to the accompanying figures, in which.

Figure 1:
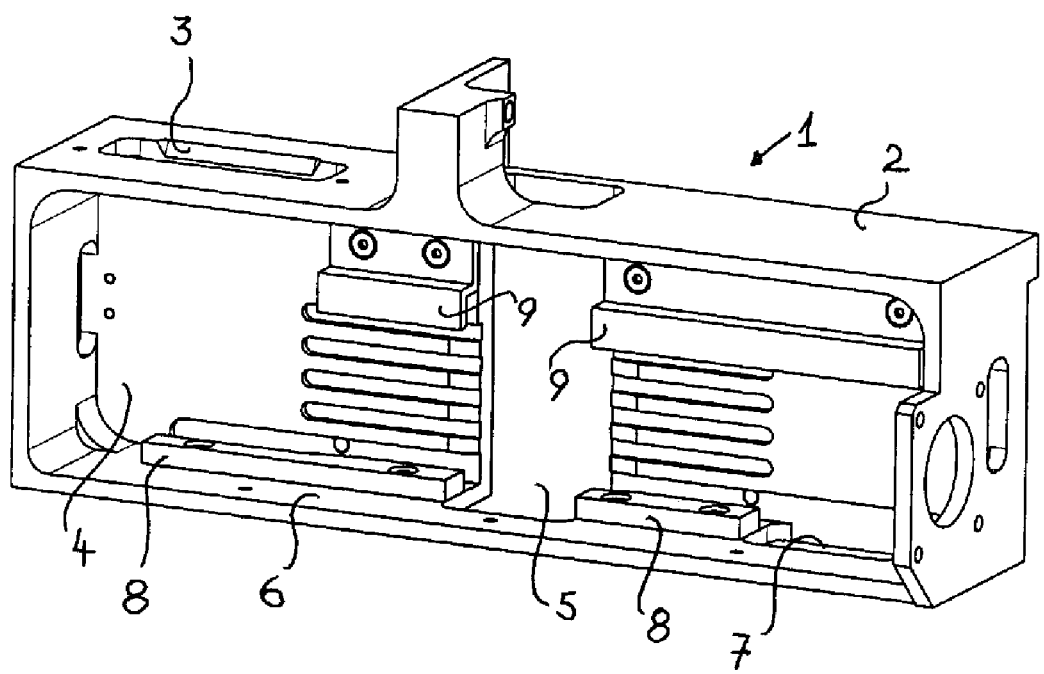
FIG. 1 illustrates a housing of a changing device according to an embodiment of the present invention, without a front wall.

Repeat use of reference characters in the present specification and drawings is intended to represent same or analogous features or elements of the invention.

DETAILED DESCRIPTION

Reference will be made in detail to certain embodiments of the invention, one or more examples of which are illustrated in the accompanying drawings.

In a housing 1 illustrated in FIG. 1, a front wall has been omitted so that it is possible to look into the inside of the housing 1. The housing 1 has a cover 2 provided with a loading opening 3. In a rear wall 4, a transfer opening 5 is provided in the form of a cut-out, which passes into a cut-out in a bottom 6 of the housing 1. In the bottom 6, moreover an unloading opening 7 is provided.

Between the area of the loading opening 3 to the transfer opening 5 and the transfer opening 5 to the unloading opening 7, guide bars 8 are arranged on the bottom 6 and guide rails 9 on the cover 2. Cassettes that are inserted into the housing 1 will slide during the transport from one opening to the other between the guide bars 8 on the bottom 6 of the housing and are held on top in the guide rails 9.

Figure 2:
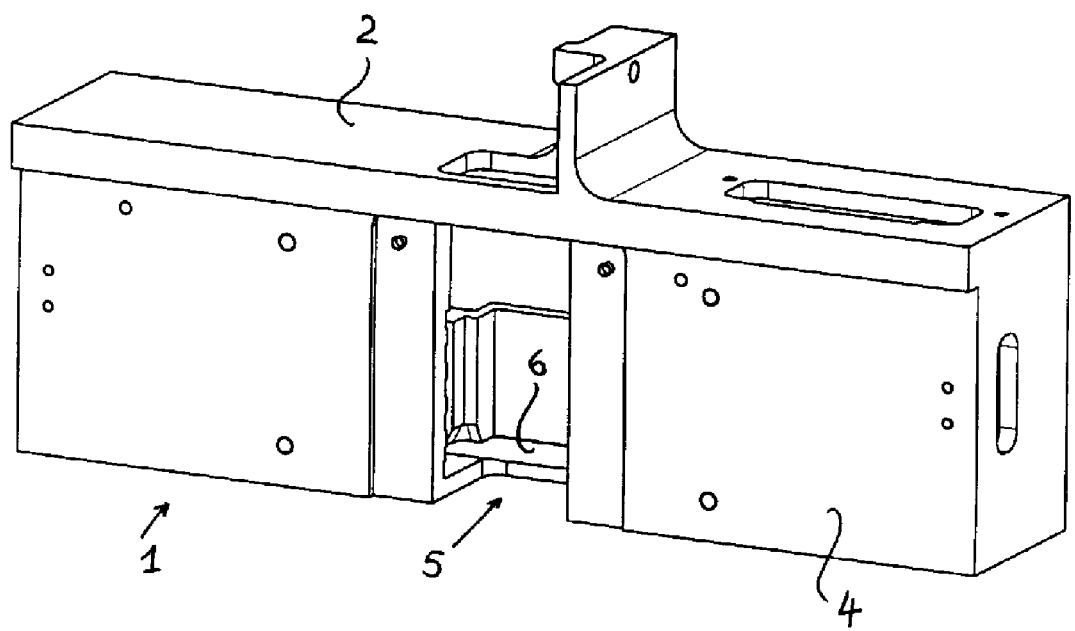
FIG. 2 is a rear view of the housing shown in FIG. 1.

From the rear view of the housing 1 illustrated in FIG. 2, the transfer opening 5 can be clearly seen, once again as a continuous cut-out in the rear wall 4 and the bottom 6.

Figure 3:
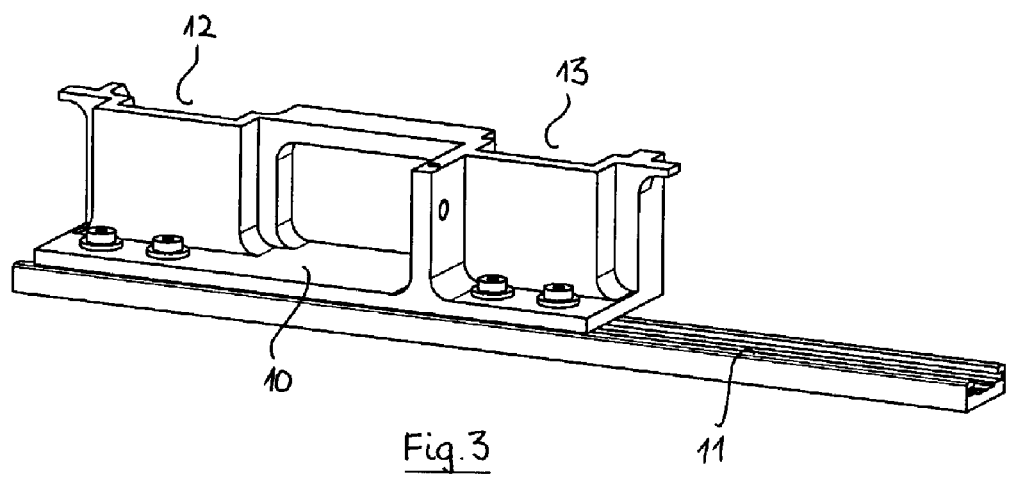
FIG. 3 is a perspective view of a slide for use with the housing shown in FIG. 1.
Figure 4:
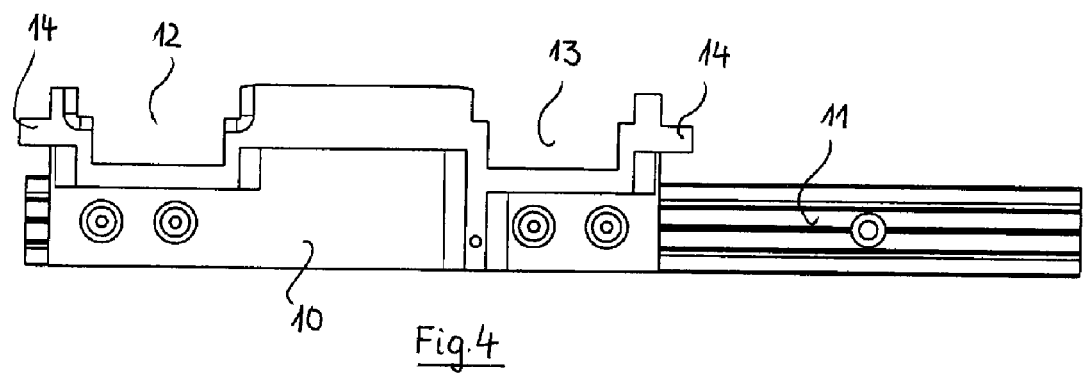
FIG. 4 is a top view of a slide shown in FIG. 3.

FIG. 3 is a view of a slide 10 which can be moved in the housing 1. The slide 10 is arranged on a rail 11 which is mounted on the bottom 6 next to the guide bars 8. The slide 10 includes a first receiving compartment 12 and a second receiving compartment 13. The receiving compartments 12, 13 are formed as frames having a U-shaped cross-section and being perpendicular to the bottom 6, as can also be taken from FIG. 4.

The slide 10 includes noses 14 which project on the left and the right side and are provided as an interrupter for a light barrier.

Figure 5:
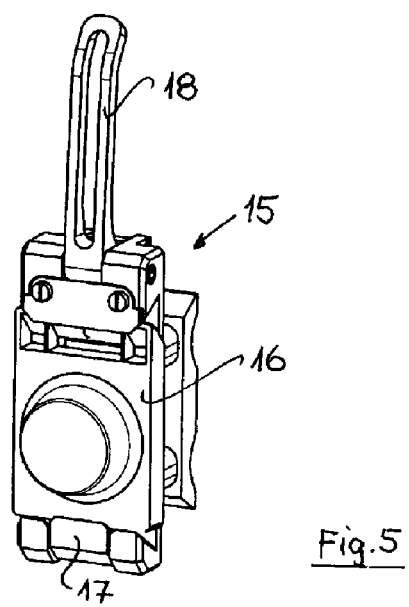
FIG. 5 shows a tensioning clamp for use with the embodiment of the changing device shown in FIGS. 1-4.

FIG. 5 shows a tensioning clamp 15, which should be understood in this art, for receiving a cassette 16. The tensioning clamp 15 includes a clamping jaw 17 which can be opened by the exertion of pressure on a lever 18. When the clamping jaw 17 is opened, the cassette 16 can be laterally inserted into the tensioning clamp 15.

Figure 6:
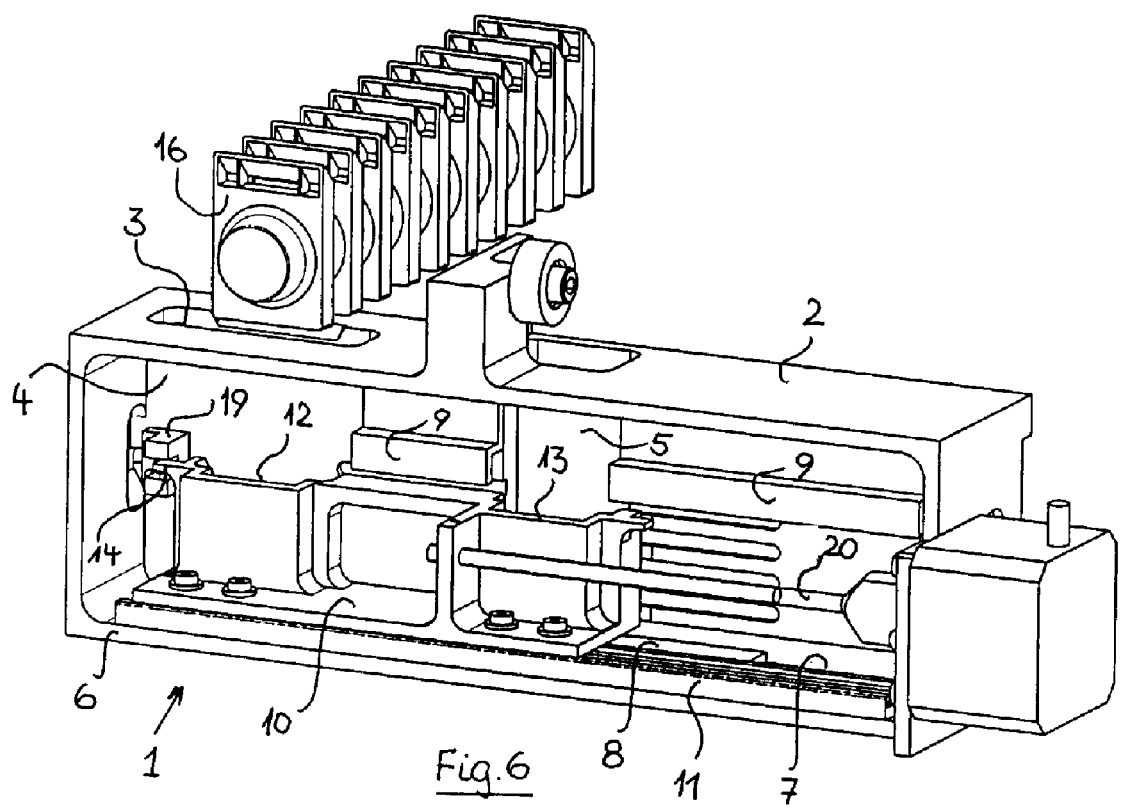
FIG. 6 shows the changing device of the embodiment shown in FIGS. 1-4, with the slide in the first end position.

FIG. 6 illustrates the operation of the changing device. The slide 10 has moved into a first end position which is set via a light barrier 19. The slide 10 is displaced by a motor-driven spindle 20. In the illustrated position of the slide 10, a cassette 16 can fall through the loading opening 3 into the first receiving compartment 12 and onto the bottom 6. In a simplified way, the cassettes 16 are illustrated in the form of a stack which can be displaced in the direction of the housing 1. In practice, they are arranged in a magazine which, in the case illustrated in FIG. 6, is arranged above the housing 1 and from the front side of which the cassettes 16 are pushed out one after the other. Of course, it is likewise possible to arrange such a magazine at the level of the bottom 6 of the housing 1 and to push the cassettes 16 into the receiving compartment 12 through a corresponding loading opening in the rear wall 4.

Figure 7:
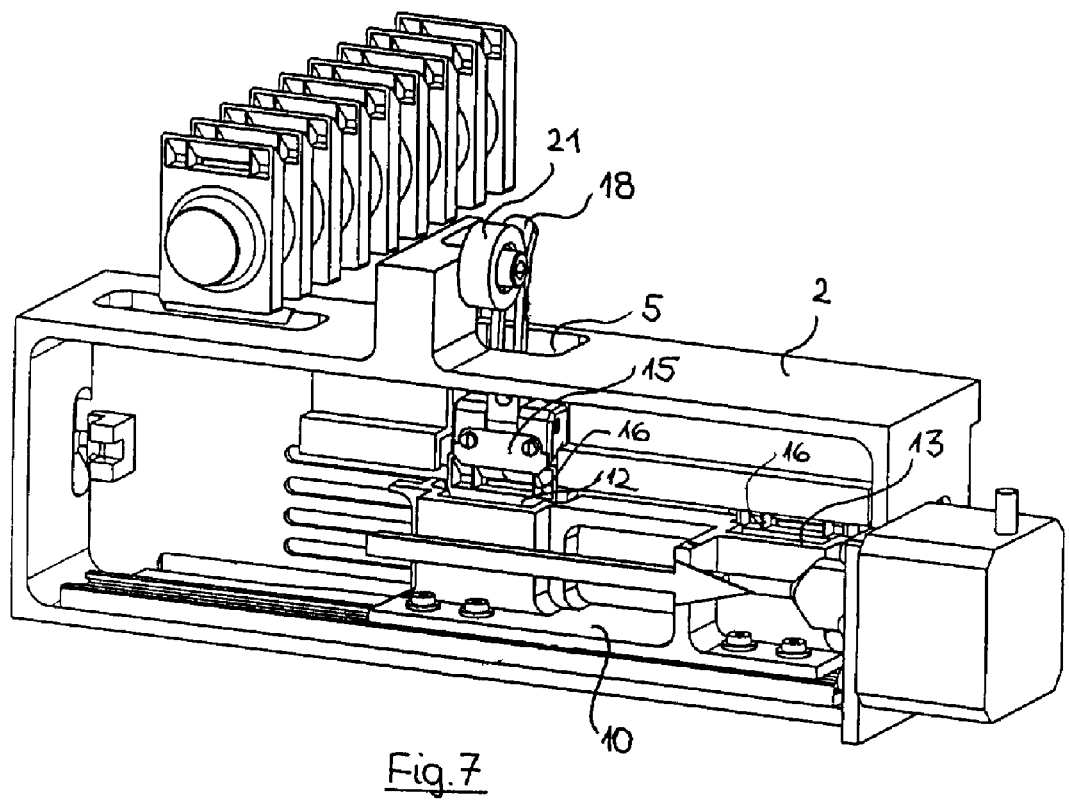
FIG. 7 shows the changing device of FIGS. 1-6, with the loaded slide in the second end position.

FIG. 7 shows the slide 10 in the second end position which is set by a non-illustrated light barrier at the right side of the housing. The first receiving compartment 12 has moved into the transfer opening 5 into which a tensioning clamp 15 has previously been moved from below. In doing so, by abutment of the lever 18 on a roll 21 mounted to the cover 2 of the housing 1, the tensioning clamp 15 has been opened. When the slide 10 is traversed in the direction indicated by the arrow, a new cassette 16 present in the receiving compartment 12 can therefore be laterally inserted into the tensioning clamp 15.

The tensioning clamp 15 can be mounted on the sample holder of, for example, a rotation microtome. By arrangement of the transfer opening 5 above the sample holder in lifting direction, an automatic sample transfer out of the changing device or into the changing device can take place given sufficient lifting height of the sample holder.

Figure 8:
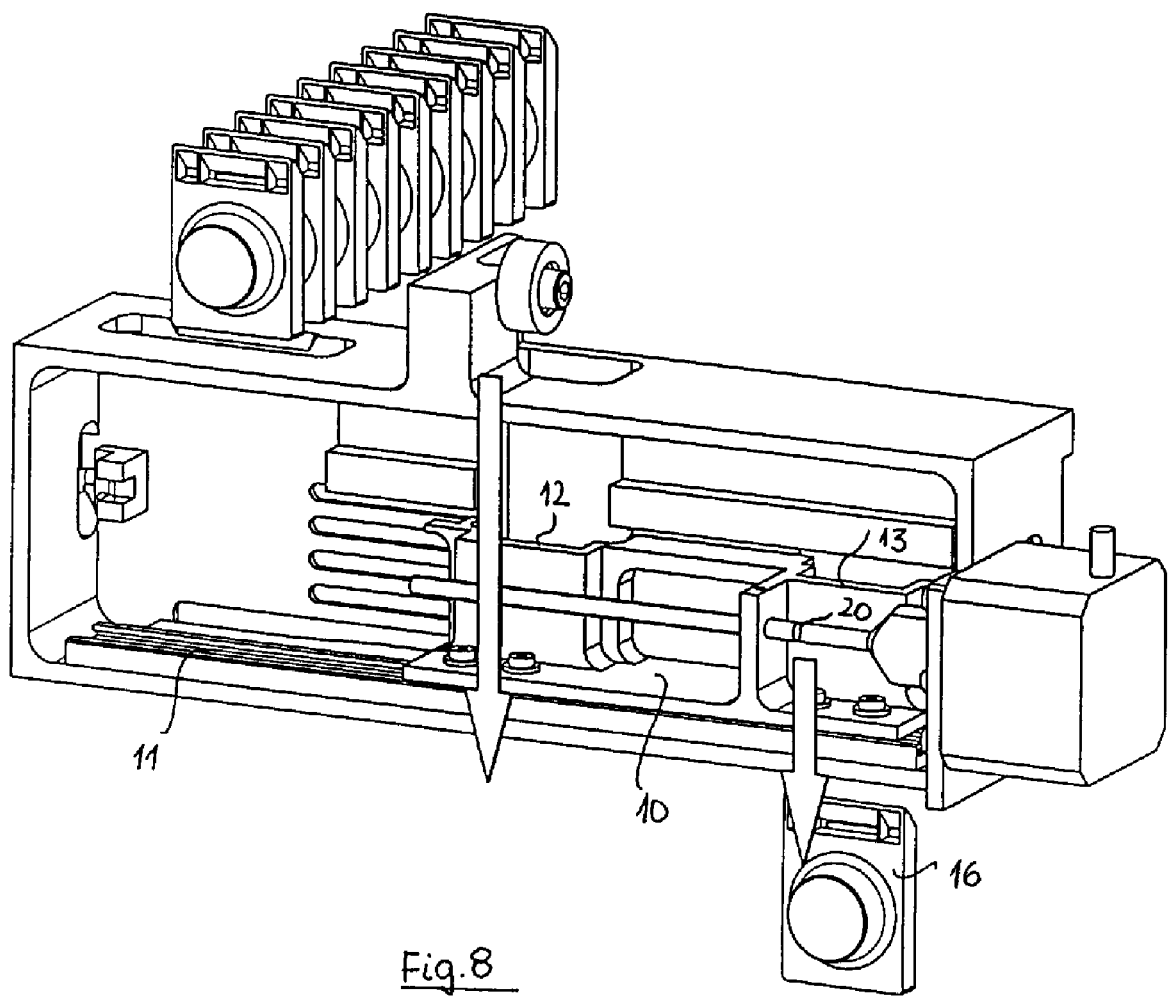
FIG. 8 shows the changing device of FIGS. 1-7, with the unloaded slide in the second end position.

The receiving compartment 13 with a processed cassette 16 stands in the illustrated second end position of the slide 10 above the unloading opening 7 arranged in the bottom 6 of the housing 1 so that the cassette can fall out downwardly through the unloading opening 7 (FIG. 8). Preferably, a magazine for receiving the processed cassettes is arranged below the unloading opening 7.

After lowering the filled tensioning clamp 15, the two receiving compartments 12, 13 are emptied (FIG. 8). The slide 10 is then returned into the first end position and can be filled with a new cassette 16 in the first receiving compartment 12. By lifting and opening the tensioning clamp 15, a processed cassette 16 can again be inserted into the second receiving compartment 13.

While one or more embodiments of the present invention have been described above, it should be understood that any and all equivalent realizations of the present invention are included within the scope and spirit thereof. Thus, the embodiments presented herein are provided by way of example only.

What is claimed is:

1. A cassette changing device for a microtome, comprising:
   a) a housing having a loading opening, a transfer opening and an unloading opening, the openings being arranged with respect to each other linearly in the housing; and
   b) a slide disposed in the housing linearly movably between a first position and a second position and having a first receiving compartment and a second receiving compartment aligned with respect to each other so that, in the first position of the slide, the first compartment and the second compartment are respectively aligned with a first two of the openings and, in the second position of the slide, the first compartment and the second compartment are respectively aligned with a second two of the openings.

2. The changing device according to claim 1, comprising a motor that moves the slide between the first position and the second position.

3. The changing device according to claim 2, comprising respective light barriers disposed in the housing so that the light barriers intercept the slide at the first position and the second position for control of the motor.

4. The changing device according to claim 1, wherein each of the first receiving compartment and the second receiving compartment is formed as an open frame having a U-shaped cross-section in a plane within which the slide shifts between the first position and the second position.

5. The changing device according to claim 1, wherein the first receiving compartment and the second receiving compartment are aligned with respect to each other so that, in the first position of the slide, the first compartment is aligned opposite the loading opening and the second compartment is aligned opposite the transfer opening, and in the second position of the slide, the first compartment is aligned opposite the transfer opening and the second compartment is aligned opposite the unloading opening.

6. The changing device according to claim 5, wherein the loading opening is arranged in a cover of the housing and wherein a cross-sectional area of the loading opening is approximately the same as a cross-sectional area of the first receiving compartment.

7. The changing device according to claim 5, wherein the loading opening is arranged in a rear wall of the housing and wherein the loading opening is a size approximately the same as an area formed by the first receiving compartment.

8. The changing device according to claim 5, wherein the first receiving compartment and the second receiving compartment have an approximately same cross-sectional area and wherein the transfer opening is formed as a continuous cut-out in a bottom and a rear wall of the housing, the cut-out in the bottom having a cross-sectional area approximately the same as the cross-sectional area of the first receiving compartment and the second receiving compartment and the cut-out in the rear wall being a size approximately the same as an area formed by each of the first receiving compartment and the second receiving compartment.

9. The changing device according to claim 5, wherein the unloading opening is arranged in a bottom of the housing and wherein a cross-sectional area of the unloading opening is approximately the same as a cross-sectional area of the second receiving compartment.

10. A method of changing a cassette in a microtome, the method comprising the steps of:
   a) providing a housing having a loading opening, a transfer opening and an unloading opening, the openings being arranged with respect to each other linearly in the housing;
   b) providing a slide linearly movable in the housing between a first position and a second position and having a first receiving compartment and a second receiving compartment aligned with respect to each other so that, in the first position of the slide, the first compartment is aligned opposite the loading opening, and the second compartment is aligned opposite the transfer opening, and in the second position of the slide, the first compartment is aligned opposite the transfer opening and the second compartment is aligned opposite the unloading opening;
   c) in the first position of the slide, filling the first receiving compartment with a first cassette through the loading opening;
   d) following step (c), moving the slide into the second position and moving the first cassette from the first receiving compartment through the transfer opening to the microtome;
   e) following step (d), moving the slide into the first position, filling the first receiving compartment with a second cassette and, after the microtome processes the first cassette, moving the first cassette into the second receiving compartment;
   f) following step (e), moving the slide into the second position, moving the first cassette from the second receiving compartment through the unloading opening, and moving the second cassette from the first receiving compartment through the transfer opening to the microtome; and
   g) following step (f), moving the slide into the first position, filling the first receiving compartment with a third cassette and, after the microtome processes the second cassette, moving the second cassette into the second receiving compartment.

* * * * *